United States Patent [19]

McWhirter et al.

[11] Patent Number: 4,751,461
[45] Date of Patent: Jun. 14, 1988

[54] METHOD OF LOCATING AND DETERMINING THE EXTENT OF CORROSION IN TUBULAR GOODS

[75] Inventors: Vernie C. McWhirter, Pearland; Thomas W. Guettinger, Houston, both of Tex.

[73] Assignee: Western Atlas International, Inc., Houston, Tex.

[21] Appl. No.: 799,225

[22] Filed: Nov. 18, 1985

[51] Int. Cl.[4] .................... G01N 27/72; G01N 27/82; G01R 33/12; G06F 15/20
[52] U.S. Cl. .................................. 324/221; 364/507
[58] Field of Search ............................... 324/219-221, 324/226, 227, 243; 364/481, 507, 552

[56] References Cited

U.S. PATENT DOCUMENTS

| | | | |
|---|---|---|---|
| 3,543,144 | 11/1970 | Walters et al. | 324/221 |
| 3,675,118 | 7/1972 | Booth | 324/226 |
| 4,144,149 | 3/1980 | Holt et al. | 324/220 |
| 4,292,589 | 9/1981 | Bonner | 324/221 |
| 4,365,198 | 12/1982 | Toth | 324/226 |
| 4,631,688 | 12/1986 | Boehm et al. | 364/481 |

OTHER PUBLICATIONS

"Dresser Atlas Casing Evaluation Services", published Aug. 1985, pp. 17–40.

Primary Examiner—Reinhard J. Eisenzopf
Assistant Examiner—Walter E. Snow
Attorney, Agent, or Firm—Patrick H. McCollum

[57] ABSTRACT

A method for determining the type of corrosion present in deteriorating pipes. An inspection instrument is passed through a length of casing to determine the extent of corrosive deterioration. The resulting measurements generated by the inspection instrument are processed to exclude those responses caused by the structural configuration of the casing length under inspection. The remaining responses of one of the measurements are then analyzed to provide useful information regarding the type of corrosion present at defects in the casing length under inspection and to further provide information necessary to make a detailed analysis of the defects present in the casing length under inspection.

10 Claims, 3 Drawing Sheets

METHOD OF LOCATING AND DETERMINING THE EXTENT OF CORROSION IN TUBULAR GOODS

BACKGROUND OF THE INVENTION

This invention relates to methods and apparatus for evaluating the condition of oilfield tubular goods and the state of deterioration of subsurface pipe or casing. More specifically, this invention relates to methods to determine whether corrosion present in the oilfield tubular goods or subsurface pipe or casing may be classified as general or isolated corrosion.

A variety of problems may result from the deterioration of subsurface casing. Drill pipe collars may rub the casing, possibly leading to a blowout if the casing is allowed to become extremely worn. In a production well, deteriorated casing may permit undesirable "thiefing" of the flow to unwanted zones, thereby reducing the surface production. In an injection well, deteriorated casing may permit the injected fluid to flow to undesired formations.

Thus, it has been a long sought goal to provide accurate information concerning the condition of subsurface casing deterioration. In production wells, this information is useful when planning repairs and workovers or perforations of new intervals in already perforated casing.

A well known method of acquiring information regarding subsurface casing conditions, specifically the determination of the presence of defects in downhole casing strings has been through the use of inspection instruments such as the one described in U.S. Pat. No. 3,543,144, issued to Walters et al on Nov. 20, 1970. The basic inspection instrument consists of an electromagnet, a magnetic sensing section, and two electronic packages to process the signals from the magnetic sensing section. During operation, a steady (DC) electromagnetic field of constant strength is generated by the inspection instrument. As the tool traverses the survey interval at a constant logging speed, the electromagnetic field permeates the casing wall with magnetic lines of flux. If there is no defect in the casing, the flux lines simply pass from one of the inspection instrument's poles, through the casing, and back to the other pole. If there is a defect in the casing wall, some of the electromagnetic field generated by the inspection instrument will "leak" out of the steel casing wall and flow around the defect. To detect such leakage, the inspection instrument includes two sets of contact shoes which survey the casing wall during a logging pass. Each shoe includes two Flux Leakage (FL) coils and two Eddy Current (EC) coils; one EC coil corresponding to each FL coil.

When an FL coil detects flux leakage (indicating a defect) the companion EC coil generates a signal if the defect is on the inside casing wall. No EC signal will be generated if the defect is on the outside casing wall. At the surface, a record is made of the greastest signal from each set of shoes. These records are commonly called FL-1, FL-2 and EC respectively. Lastly, all FL signals from one set of shoes are further processed to yield a fourth recorded signal, FL AVE.

Of the four signals that can be recorded from this process, the two flux leakage signals, FL-1 and FL-2, are used to quantify the defect, or in other words, determine the percent of casing wall penetration in a defect. The third signal, EC, is used to qualify the defect to determine whether a defect is on the inside or outside of the casing wall. The fourth signal, FL AVE, is used to give an indication of the percent of the casing circumference that a defect occupies.

In order to interpret the information received from the inspection instrument and fully analyze the condition of the subsurface casing condition, considerable time and effort must be expended in the analysis of the recorded data. One problem that slows the interpretation of the data is that the structural configuration of the casing affects the existing data received from the inspection instrument. Each pipe collar, as well as hardware such as a centralizer, scratcher, or perforation, present along the casing length under inspection causes an undesirable response in the data received from the inspection instrument. These responses must be located and excluded from further analysis in order for the proper analysis of the state of casing deterioration to be made. To accomplish this analysis, visual inspection of the data provided by the inspection instrument and point-by-point comparison of the data recordings must be performed. Casing collars, centralizers, perforations and scratchers must be identified by the visual inspection of the responses of the received data and eliminated from the casing corrosion analysis.

Generally, data responses which have not been eliminated by the above described analysis are classified as defects caused by corrosion. There are two basic types of corrosion that may be present at the located defect: general corrosion and isolated corrosion. Isolated corrosion is commonly considered to be a defect or pit limited in extent to several inches in diameter vertically along the casing string as well as circumferentially around the casing. General corrosion, on the other hand, is often characterized by numerous, closely spaced defects extending over several feet vertically along the casing or circumferentially around the casing or both.

As well as being a useful indicator of the condition of subsurface casing or similar tubular goods, the discrimination between general and isolated corrosion is necessary for further corrosion analysis. A common step in the analysis of casing defects caused by corrosion is the use of the FL response, which indicates the presence of a defect, in calculating the percent casing wall penetration for that defect. Typically, this calculation is made by using the appropriate casing penetration chart. Choice of the proper casing penetration chart for this calculation is made by considering whether the corrosion present at the defect is general or isolated corrosion, whether the defect is located along the inside or the outside of the casing as well as the casing's outside diameter, weight-per-foot, and grade.

SUMMARY OF THE INVENTION

An inspection instrument is passed through a length of casing to determine the extent to which corrosive deterioration of the casing length under inspection has occurred. The inspection instrument generates four data measurements and delivers these data measurements to the surface facility for recording. Of these four data measurements, the first two (FL-1 and FL-2) are used to quantify the casing defect due to corrosion. The third measurement, EC, is used to qualify the defect, and the fourth measurement, FL AVE, is used to indicate the circumferential extent of that defect. Since the structural configuration of the casing length under inspection affects the data responses received from the inspection instrument, the data responses caused by defects in the casing due to corrosion and the data responses caused by the structural configuration of the casing must be separated.

The present invention analyzes the data from the inspection instrument and processes the data to exclude those data reponses caused by the casing's structural configuration from any further analysis as defects caused by casing corrosion. The remaining data responses of the FL AVE measurement, which are considered indicators of casing defects caused by corrosion, are then processed to create a general corrosion activity curve for the casing by averaging the responses of the FL AVE measurement along a series of intervals of selected length. The general corrosion activity curve may then be anayzed to determine whether the corrosion present at defects along the casing length under inspection may be classified as general or isolated corrosion.

A feature of this invention is to allow the classification of the corrosive deterioration of casing as general corrosion or isolated corrosion. Another feature of this invention is to provide information necessary to the calculation of a quantitative assessment of the degree of casing wall penetration due to corrosive deterioration. Yet another feature of this is to provide information regarding downhole casing corrosion as quickly and as accurately as possible.

BRIEF DESCRIPTION OF THE DRAWINGS

The present invention may be better understood and its numerous objects and advantages will become apparent to those skilled in the art by reference to the accompanying drawings.

DESCRIPTION OF THE PREFERRED EMBODIMENT OF THE INVENTION

Figure 1:
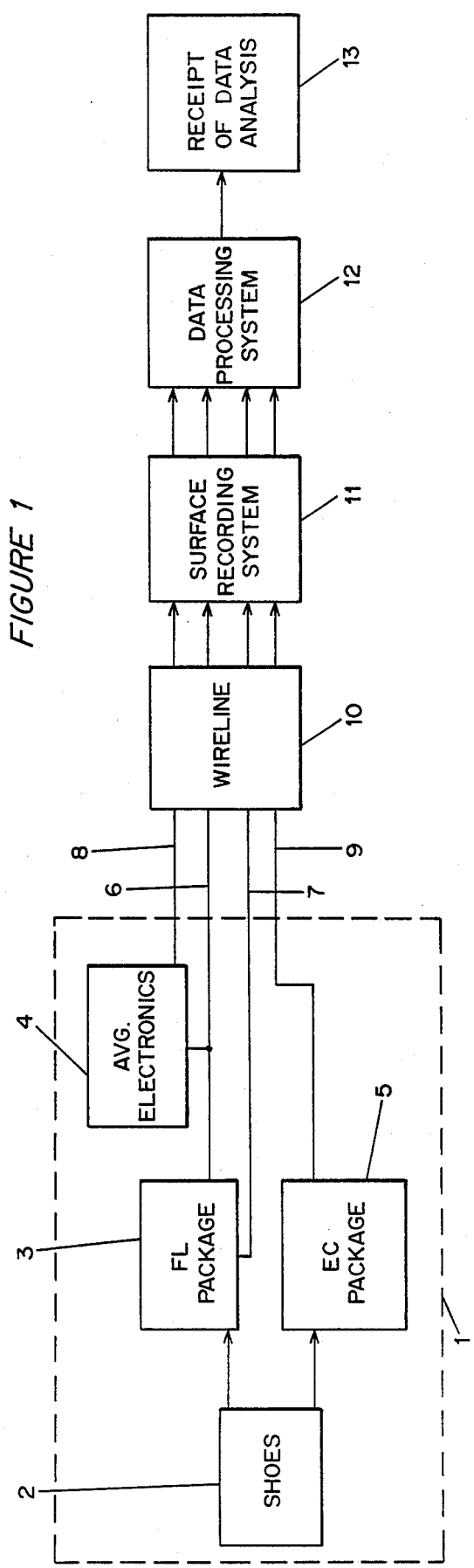
FIG. 1 is a generalized block diagram showing the path of the data under inspection in an embodiment of the method according to the invention for the evaluation of the state of deterioration of downhole casing.

Referring to FIG. 1, within the inspection intrument 1 electromagnetic signals from the shoes 2 are processed by the FL electronics package 3 which generates the data series FL-1 6 and FL-2 7. The averaging electronics package 4 further processes the data series FL-1 to generate the data series FL AVE 8. The EC electronics package 5 processes additional electromagnetic signals from the shoes 2 to generate the data series EC 9. After generation, the data series FL-1, FL-2, FL AVE, and EC are transmitted from the inspection instrument 1 via the wireline 10 to the surface recording system 11. After recording by the surface recording system 11, the data series FL-1, FL-2, FL AVE, and EC are tranferred from the surface recording system 11 to the data processing system 12. The data processing system 12 interprets the recorded data series FL-1, FL-2, FL AVE, and EC and prepares a detailed analysis of the condition of the casing length under inspection for transmission from the data processing system 12 to the surface operator at 13. A more detailed description of the operation of inspection instrument 1 can be found in U.S. Pat. No. 3,543,144 which is incorporated herein by reference.

Figure 2:
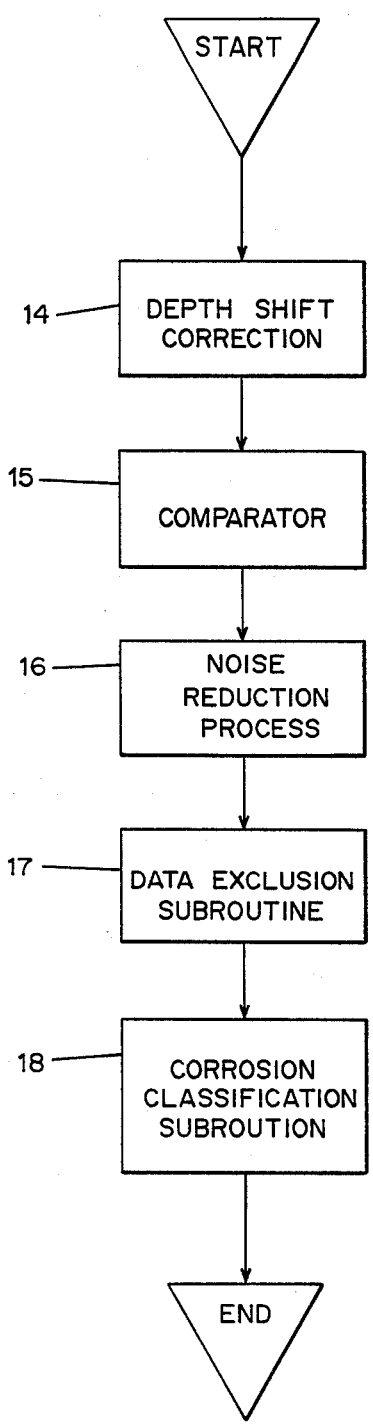
FIG. 2 is a flowchart of the major steps of the method of processing the data measurements received from the casing inspection instrument.

Referring to FIG. 2, the data processing system 12 of FIG. 1 is described in greater detal. The data series FL-1, FL-2, FL AVE, and EC are first subjected to depth shift correction 14. Depth shift is a delay in the receipt of data caused by the inspection instrument during the generation of the data series. The extent of the depth shift is readily determined and a correction factor designated. Data series FL-1 and FL-2 are then subjected to a comparator 15 which combines data series FL-1 and FL-2 into a single data series FL with duplicate signals removed. Data series FL, FL AVE and EC are then subjected to a noise reduction process 16 which compares the data series FL, FL AVE, and EC to a noise threshold value. If a point on the data series is deterined to be less than the noise threshold value, that point is set equal to zero. Otherwise, the data point is left unchanged. The new data series resulting from the noise reduction process are FLS, FAVS and ECS. Data series FLS, FAVS and ECS are then subjected to the data exclusion subroutine 17 which edits FLS, FAVS and ECS to remove those responses which are caused by the structural configuration of the casing length under inspection. The edited data series FAVS is then subjected to a corrosion classification subroutine 18 which performs a series of manipulations of the received data while preparing an analysis of the type of corrosion present for the casing length under inspection.

Figure 3:
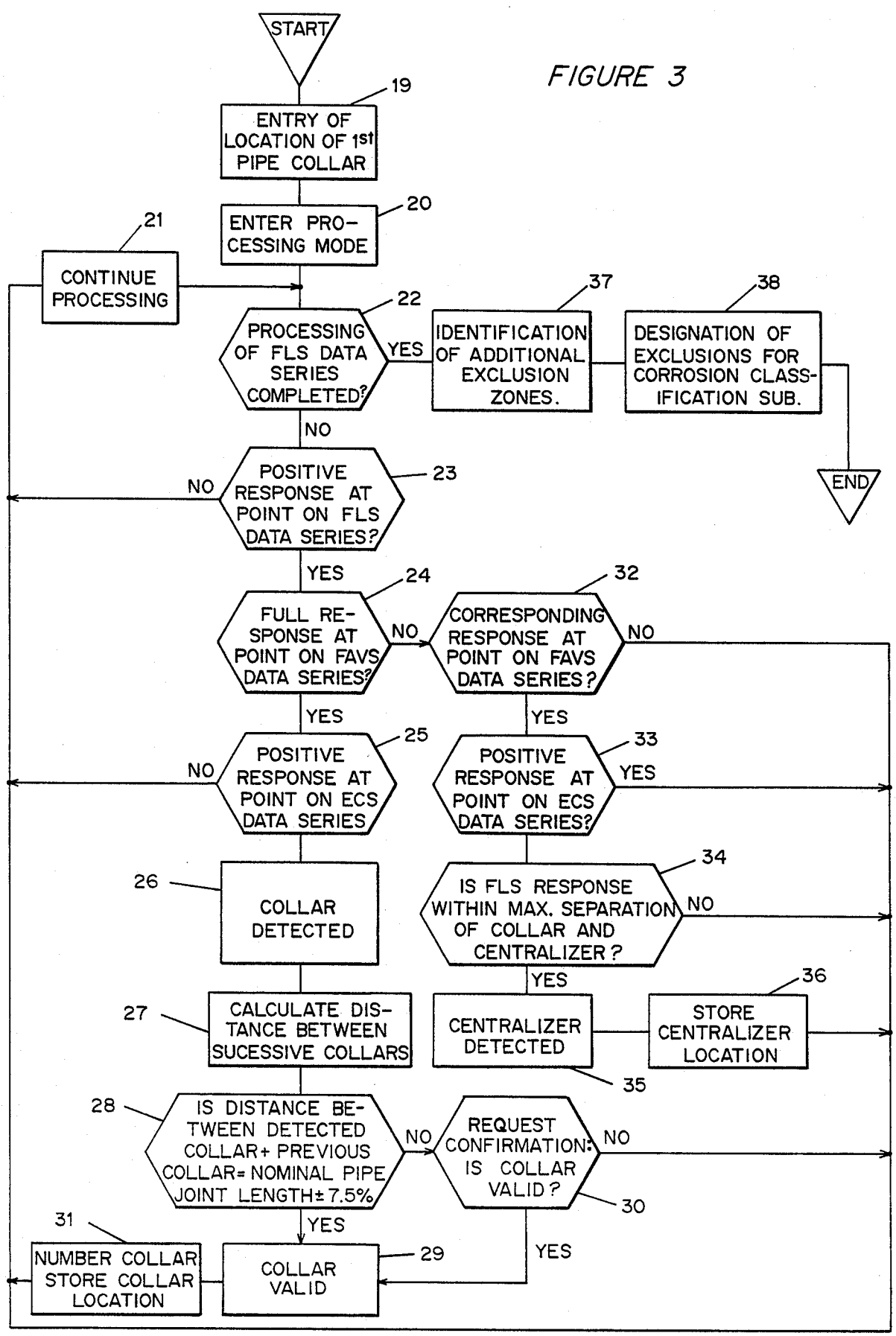
FIG. 3 is a more detailed flowchart of the data exclusive subroutine step of the flowchart of FIG. 2.

Referring to FIG. 3, a detailed block diagram of the data exclusion subroutine 17 is shown. The subroutine is first synchronized to the location of the first pipe collar at 19. The subroutine enters the processing mode at 20. In the processing mode, the FLS data series is searched for responses. The subroutine will exit the processing mode at 22 when the subroutine detects that the entire FLS data series has been processed. The subroutine searches a point on the FLS data series for a response at 23. If no FLS response is detected at 23, then the subroutine will continue processing the successive point of the FLS data series at 21. If an FLS response is detected at 23, then the corresponding point of the FAVS data series will be examined at 24. If the response of the FAVS data series at the corresponding point is considered a full response (a "full" response being defined as a response with magnitude approximately equivalent to the magnitude of the response at the first pipe collar), then the related point of the ECS data series will be examined at 25. If the ECS response is detected at 25, then the subroutine will declare a detected collar at 26. If no ECS response is detected at 25, then the subroutine will return to 21 to continue processing the successive point of the FLS data series. If the subroutine declares a detected collar at 26, then the distance between the detected collar and the previous collar will be calculated at 27. If the distance between the detected collar and the previous collar is found at 28 to be within 7.5% of the preset nominal pipe joint length, then the collar is declared valid at 29. If the distance between the detected collar and the previous collar varies from the nominal pipe joint length by more than 7.5%, then confirmation of the collar will be requested at 30. If the collar is confirmed at 30 then the collar will be declared valid at 29. If no confirmation of the detected collar is made at 30, then the subroutine will return to 21 for processing of the successive point of the FLS data series. If the subroutine has declared a valid collar at 29, then the collar will be numbered and its location stored at 31. The length of casing between two such collars is termed a casing joint. The subroutine will then return to 21 for processing of the successive point of the FLS data series.

Returning to step 24 of the subroutine, if the response of the FAVS data point is not considered a full response, then the FAVS response will be compared at 32 to a corresponding response for a centralizer (a "corresponding" response is generally considered a response of substantial magnitude but which is of noticeably less magnitude than a "full" response). If there is no corresponding FAVS response at 32, then the subroutine will return to 21 for processing of the successive point of the FLS data series. If a corresponding FAVS response is detected at 32, then the related point of the ECS data series will be examined at 33. If there is an ECS response at 33, then the subroutine will return to 21 for processing of the successive point of the FLS data series. If there is no ECS response detected at 33, then the subroutine will determine at 34 whether the FLS response is within the entered maximum separation between a collar and a centralizer. If the FLS response is within the maximum separation between a collar and a centralizer, then the subroutine declares a detected centralizer at 35, stores the centralizer location at 36, and return to 21 for further processing. If the FLS response is not within the maximum separation, then no centralizer is declared and the subroutine will return to 21 for further processing.

Upon completion of processing of the FLS data series at 22, the subroutine will then permit identification at 37 of additional data to be excluded from the corrosion classification subroutine 18. The subroutine then designates at 38 all centralizers, collars, and other designated portions of the data series as exclusion zones. Any responses within the exclusion zones will not be considered as possible defects during the corrosion classification subroutine 18.

Figure 4:
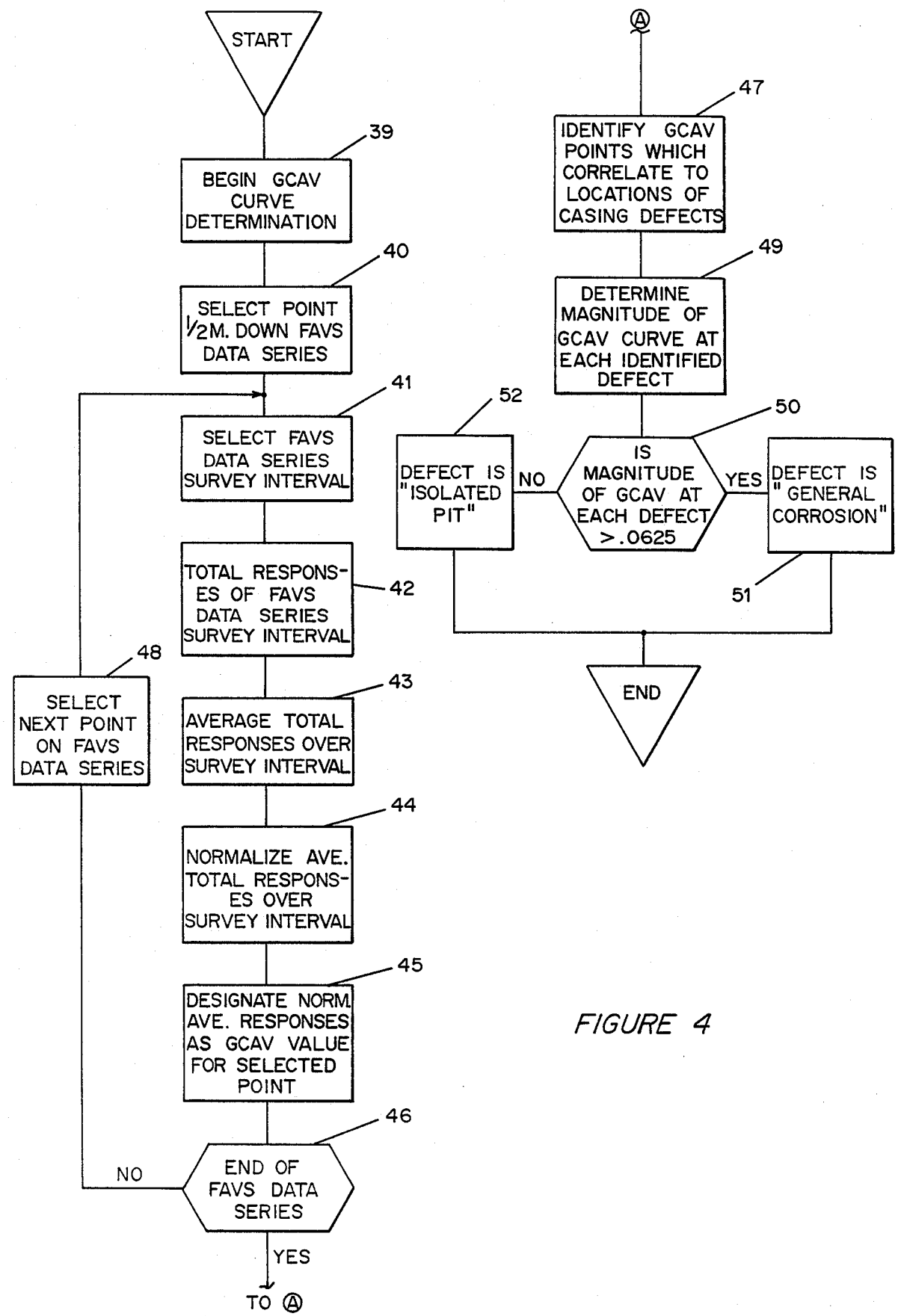
FIG. 4 is a more detailed flowchart of the corrosion classification subroutine step of the flowchart of FIG. 2.

Referring to FIG. 4, a detailed block diagram of the corrosion classification subroutine 18 is shown. Corrosion classification subroutine 18 starts at 39 by initiating the determination of the general corrosion activity ("GCAV") curve. The GCAV cruve comprises a series of data points, each data point being a determination of the responses of FAVS averaged over a selected interval. While any size response survey interval may be selected, it has been found that an interval of 1 meter works quite well.

A point located a distance of one-half of the selected survey interval length from the top of the FAVS data series is selected by the subroutine at 40. A section of the FAVS data series of length equal to the selected survey interval length with the point designated in step 40 as the midpoint of the section of the FAVS data series is designated as the selected interval at 41. The combined responses of the selected interval of the FAVS data series are determined at 42. The combined responses of the selected interval of the FAVS are then averaged over the selected interval at 43 to calculate the average response of the FAVS data series for the selected interval. The subroutine then normalizes the average response of the FAVS data series over the selected interval at 44 by setting the maximum FAVS response at a collar equal to one and reducing the value of the average response of the FAVS data series over the selected interval proportionately. The normalized average response of the FAVS data series for the selected interval is designated at 45 as the value for the GAV curve at the selected point. If the subroutine then detects at 46 that the processing of the FAVS data series and the calculation of the GCAV curve is complete, then the subroutine will begin to classify the extent of the corrosion of the casing at 47. If the processing of the FAVS data series and calculation of the GCAV curve are not complete at 46, the subroutine will select the next point of the FAVS data series to be examined at 48 and the subroutine will return to step 41 to continue the processing of the FAVS data series and the GCAV curve.

Returning to step 47, the classification of the extent of the corrosion of the casing under inspection begins by identifying those points on the GCAV curve which correlate to defects in the casing caused by corrosion. Identification of casing defects caused by corrosion may be made through the methods disclosed in the copending application Ser. No. 799,226. The magnitude of the GCAV curve at each of the casing defects is then determined at 49. If the magnitude of the GCAV curve response at a casing defect is determined at 50 to exceed a preselected reference value, in the preferred embodiment 0.0625, the defect is designated at 51 as a defect caused by general corrosion of the casing. Otherwise, the defect is classified at 52 as a defect caused by an isolated pit in the casing.

Thus, there has been described and illustrated herein methods for determining the presence of general and isolated corrosion in tubular goods. However, those skilled in the art will recognize that many modifications and variations besides those specifically mentioned may be made in the techniques described herein what departing substantially from the concept of the present invention. Accordingly, it should be clearly understood that the form of the invention described herein is exemplary only, and is not intended as a limitation on the scope of the present invention.

The embodiments of the invention in which an exclusive property or privilege is claimed are defined as follows:

1. A method of classifying the type of corrosion present in a length of subsurface casing under inspection, including structural elements, by passing an inspection instrument through said casing and submitting the outputs of said inspection instrument to a process of analysis comprising the following machine implemented steps:
    a. deriving a first measurement from said inspection instrument;
    b. determining points on said first measurement representing structural elements of said length of casing;
    c. analyzing said first measurement to calculate a series of data points;
    d. adjusting said series of data points in respect of the presence of said structural elements on said length of casing;
    e. combining said series of data points; and
    f. analyzing said series of data points to determine the extent of corrosion of said casing length under inspection.

2. The method of claim 1 wherein the step (c) above of analyzing said first measurement to calculate a series of data points further comprises the following steps:
    g. selecting a first point on said first measurement;

h. selecting a first interval of said first measurement such that said first point is the midpoint of said first interval;

i. averaging the responses of said first interval of said first measurement to calculate, at said midpoint, a new data point; and j. repeating steps (g) through (i) for each data point of said first measurement.

3. The method of claim 1 wherein the step (f) above of analyzing said series of data points to determine the extent of corrosion of said casing length under inspection further comprises the following steps:

k. calculating the magnitude of said series of data points;

l. comparing the magnitude of said series of data points to a preselected reference value; and m. classifying the areas of corrosion present for said casing length under inspection.

4. A method of classifying the type of corrosion present at defects located while inspecting a length of casing, containing other structural elements, by passing an inspection instrument through said casing and submitting the outputs of said inspection instrument to a process of analysis comprising the following machine-implemented steps:

a. deriving a first measurement from said inspection instrument;

b. determining points on said first measurement representing structural elements of said length of casing;

c. analyzing said first measurement to calculate a series of data points;

d. adjusting said series of data points in respect of the presence of said structural elements on said length of casing;

e. combining said series of data points; and f. analyzing said data points correlating to said defects in said casing to classify the type of corrosion present at said defects.

5. The method of claim 4 wherein the step (c) above of analyzing said first measurement to calculate a series of data points further comprises the following steps:

g. selecting a first point on said first measurement;

h. selecting a first interval of said first measurement such that said first point is the midpoint of said first interval;

i. averaging said responses of said first interval to calculate, at said midpoint, a new data point; and j. repeating steps (g) through (i) for each data point of said first measurement.

6. The method of claim 4 wherein the step (f) above of analyzing said data points correlating to said defects in said casing to classify the type of corrosion present at said defects further comprises the following steps:

k. calculating the magnitude of said data points correlating to said defects in said casing; and l. classifying said type of corrosion at said defects based on the magnitude of said data point.

7. The method of claim 6 wherein the step (l) above of classifying said type of corrosion at said defects based on the magnitude of said data points further comprises the following steps:

m. comparing the magnitude of a first data point to a preselected reference value;

n. classifying said type of corrosion at a first defect as general corrosion if said magnitude of said first data point correlating to said first defect exceeds said preselected reference value;

o. classifying said type of corrosion at said first defect as isolated corrosion if said magnitude of said first data point correlating to said first defect fails to exceed said preselected reference value; and p. repeating steps (m) through (o) above for each of said defects.

8. A method of classifying the type of corrosion present at a defect located while inspecting a length of casing, containing structural elements, by passing an inspection instrument through said casing and submitting the outputs of said inspection instrument to a process of analysis comprising the following machine-implemented steps:

a. deriving a first measurement from said inspection instrument;

b. determining points on said first measurement representing structural elements of said length of casing;

c. identifying a point of said first measurement correlating to a defect in said casing;

d. selecting an interval of said first measurement such that said point is the midpoint of said interval;

e. averaging the responses of said interval; and f. adjusting the averaged response of said interval in respect of the presence of said structural elements on said length of casing;

g. assigning said adjusted response of said interval to said midpoint;

h. analyzing said adjusted response of said interval to identify the type of corrosion present at said defect.

9. The method of claim 8 wherein the step (h) above of analyzing the adjusted response of said interval to identify the type of corrosion present at said defect further comprises the following steps:

i. calculating the magnitude of said adjusted response;

j. classifying said type of corrosion at said defect based on said magnitude of said adjusted response.

10. The method of claim 9 wherein the step (j) above of classifying said type of corrosion at said defect based on said magnitude of said adjusted response further comprises the following steps:

k. comparing said magnitude of said adjusted response to a preselected reference value;

l. classifying said type of corrosion at said defect as general corrosion if said adjusted response exceeds said preselected reference value; and m. classifying said type of corrosion at said defect as isolated corrosion if said adjusted response fails to exceed said preselected reference value.

* * * * *